United States Patent [19]

Wyllie

[11] Patent Number: 4,701,462

[45] Date of Patent: Oct. 20, 1987

[54] METHOD FOR PREVENTION OF HYPERTENSION

[75] Inventor: Michael G. Wyllie, Canterbury, United Kingdom

[73] Assignee: John Wyeth and Brother Limited, Maidenhead, England

[21] Appl. No.: 846,313

[22] Filed: Mar. 31, 1986

Related U.S. Application Data

[63] Continuation-in-part of Ser. No. 677,251, Dec. 3, 1984, abandoned.

[30] Foreign Application Priority Data

Sep. 11, 1984 [GB] United Kingdom ................ 8422924

[51] Int. Cl.$^4$ ........................................... A61K 31/445
[52] U.S. Cl. .................................................. 514/323
[58] Field of Search ........................................ 514/323

[56] References Cited

U.S. PATENT DOCUMENTS 3,527,761  9/1970  Archibald et al. .................. 260/293
4,428,954  1/1984  Cavalla et al. ...................... 424/263

FOREIGN PATENT DOCUMENTS 1218570  1/1971  United Kingdom .

OTHER PUBLICATIONS

J. W. Woods, "Hypertension", pp. 219-223, *Current Therapy 1981* (W. B. Saunders Co., 1981).
Julius and Hansson, "Classification of Hypertension," Chapt. 44, pp. 679-682, in Genest, Jacques et al., *Hypertension: Physiopathology and Treatment*, 2nd ed, (Mac-Graw-Hill Book Co., New York, 1983).
J. L. Marx, Science, 212, 1255-57 (1981).
J. L. Archibald, "Indoramin", pp. 161-177, *Pharmacology of Antihypertensive Drugs* A. Scriabine, ed., (Raven Press, New York, 1980).
Cross et al., Br. J. of Pharm., 81, 191P (1984).
Fairhurst et al. Br. J. of Pharm., 81, 366 P (1984).

Primary Examiner—Allen J. Robinson
Attorney, Agent, or Firm—Arthur G. Seifert

[57] ABSTRACT

This invention provides a method for preventing the development of hypertension in a non-hypertension animal, including a human, having an elevated natriuretic hormone level, which comprises administering to said animal an amount of indoramin or a pharmaceutically acceptable salt thereof effective to lower the natriuretic hormone level.

1 Claim, No Drawings

METHOD FOR PREVENTION OF HYPERTENSION

This application is a continuation-in-part application of co-pending U.S. application Ser. No. 677,251, filed Dec. 3, 1984 (now abandoned).

This invention relates to a novel method for the prevention of hypertension, more particularly to a treatment of elevated natriuretic hormone levels.

In U.K. patent specification No. 1,218,570 there are described and claimed a class of indole derivatives which have various pharmacological activities, especially action on the cardiovascular system. One of these compounds, 3-[2-(benzamido-1-piperidyl)ethyl]indole, has demonstrated valuable antihypertensive properties in human beings in clinical trials. This compound has the internationally approved name: indoramin. I have now found that indoramin also possesses the ability to lower natriuretic hormone levels.

Recent research has shown that high natriuretic hormone levels have a causative link with the genesis of hypertension—see for example Science Vol. 212 pps. 1255–1257. Evidence suggests that natriuretic hormone alters cellular sodium and potassium ion transport. This cation transport system involves a "pump" using energy released during the hydrolysis of adenosine triphosate by an enzyme called sodium—dependent adenosinetriphosphatase ($Na^+$, $K^+$-ATPase). Natriuretic hormone apparently works by inhibiting this enzyme not only in the kidney but in a variety of other tissues including arterial smooth muscle. In this way the hormone forms a link between excessive dietary salt and high blood pressure. Accordingly, by its ability to lower natriuretic hormone levels, indoramim is indicated as treatment for the prevention of hypertension in those normotensives at risk with elevated natriuretic hormone levels.

Accordingly, this invention provides a method for preventing the development of hypertension in a non-hypertensive animal, including a human, having an elevated natriuretic hormone level, which comprises administering to said animal an amount of indoramin or a pharmaceutically acceptable salt thereof effective to lower the natriuretic hormone level.

This invention further provides a method for lowering elevated natriuretic hormone levels in a non-hypertensive animal, including a human, which comprises administering to an animal so afflicted an amount of indoramin or a pharmaceutically acceptable salt thereof effective to lower the natriuretic hormone level.

The effect of indoramin on natriuretic hormone levels has been examined in a number of separate experiments either directly by measurement of natriuretic hormone levels or indirectly by measuring tissue $Na^+/K^+$-ATPase activity. The latter is in inverse relationship with natriuretic hormone levels.

The following test procedure was used to measure rat brain $Na^+$, $K^+$-ATPase activity in control, spontaneously hypertensive rats and spontaneously hypertensive rats treated with indoramin. 6 male rats were used in each of these studies. Homogenates (10% w/v is 0.32M sucrose) of kidney or cerebral cortex were prepared. These were assayed undiluted. $Na^+$, $K^+$-ATPase activity was measured spectrophotometrically according to the method of Gilbert and Wyllie, Biochem. Pharmac. 24,551 (1975).

The results obtained are shown below:

| Animals tested | Rat brain $Na^+$,$K^+$—ATPase activity-$1_h^{\mu}$-1 mol Pi · mg protein | |
|---|---|---|
| | Experiment 1 | Experiment 2 |
| Control rats | 4.7 | 4.9 |
| Spontaneously hypertensive rats | 2.1 | |
| Spontaneously hypertensive rats treated with indoramin (100 mg/kg, po 14 days) | | 3.8 |

These results show that untreated hypertensive rats have an impliedly high level of natriuretic hormone and indoramin possesses the ability to reduce these implied high levels.

In another experiment a group of human volunteers having clinically significant hypertension (untreated) were examined before and after treatment with indoramin 25 mg. b.d. for 4 weeks. The following test procedure was used: the mean arterial pressures [i.e. diastolic pressure $+\frac{1}{3}$ (systolic-diastolic)] of 8 untreated hypertensive human volunteers were measured in the normal way. Immediately following the measurement of blood pressure a 10 ml sample of whole blood was removed from each volunteer and assayed for natriuretic hormone level using the radioreceptor method (3H-ouabain displacement method). Initial and final mean blood pressures for this group and initial and final mean natriuretic hormone levels are tabulated below:

| No. of patients | Mean arterial pressure (mmHg) | | Natriuretic Hormone level (ouabain-like units nM) | |
|---|---|---|---|---|
| | Pre- | Post-treatment | Pre- | Post-treatment |
| 8 | 127 ± 3 | 117 ± 5 | 16.3 ± 1.2 | 14.1 ± 0.9 |

These results show that in humans antihypertensive doses of indoramin lower natriuretic hormone levels.

When used in the methods of this invention, indoramin or a pharmaceutically acceptable acid addition or quaternary ammonium salt thereof may be administered alone or in the form of a pharmaceutically acceptable composition. Suitable carriers are well known in the art. The particular dosage will depend on the chosen route of administration and standard pharmaceutical practice. Preferrably the composition is in unit dosage form, e.g. tablets or capsules. When used in the methods of the invention, indoramin may be administered orally or parenterally. Parental administration includes, but is not limited to, intravenous, intraperitoneal, intramuscluar, or subcutaneous administration. Oral administration is preferred.

Based on the experiments detailed herein above, indoramin can be administered in antihypertensive doses to produce the desired effect on natriuretic hormone levels. Accordingly, a dose regimen of about 1 to 200 mg/day may be used for treating non-hypertensive humans suffering from elevated natriuretic hormone levels.

I claim:

1. A method for lowering elevated natriuretic hormone levels in a non-hypertensive mammal, including a human, which comprises administering to a non-hypertensive mammal having an elevated natriuretic hormone level an amount of indoramin, or a pharmaceutically acceptable salt thereof, effective to lower the natriuretic hormone level.

* * * * *